(12) United States Patent
Zhang et al.

(10) Patent No.: US 9,168,253 B2
(45) Date of Patent: Oct. 27, 2015

(54) QUINAZOLINE COMPOUNDS

(75) Inventors: Weihan Zhang, Shanghai (CN); Wei-Guo Su, Shanghai (CN); Haibin Yang, Shanghai (CN); Yumin Cui, Shanghai (CN); Yongxin Ren, Shanghai (CN); Xiaoqiang Yan, Shanghai (CN)

(73) Assignee: HUTCHISON MEDIPHARMA LIMITED, Shanghai (CN)

( * ) Notice: Subject to any disclaimer, the term of this patent is extended or adjusted under 35 U.S.C. 154(b) by 250 days.

(21) Appl. No.: 13/807,460

(22) PCT Filed: May 25, 2011

(86) PCT No.: PCT/CN2011/074637
§ 371 (c)(1),
(2), (4) Date: Mar. 15, 2013

(87) PCT Pub. No.: WO2012/000356
PCT Pub. Date: Jan. 5, 2012

(65) Prior Publication Data
US 2013/0172373 A1      Jul. 4, 2013

(30) Foreign Application Priority Data
Jun. 30, 2010   (WO) ................ PCT/CN2010/074792

(51) Int. Cl.
| *A61K 31/517* | (2006.01) |
| *C07D 239/94* | (2006.01) |
| *A61K 45/06* | (2006.01) |
| *C07D 487/04* | (2006.01) |

(52) U.S. Cl.
CPC ............... *A61K 31/517* (2013.01); *A61K 45/06* (2013.01); *C07D 239/94* (2013.01); *C07D 487/04* (2013.01)

(58) Field of Classification Search
CPC .. C07D 239/94; C07D 487/04; A61K 31/517; A61K 45/06
See application file for complete search history.

(56) References Cited

U.S. PATENT DOCUMENTS

2010/0009958 A1*   1/2010   Zhang et al. ............. 514/210.16

FOREIGN PATENT DOCUMENTS

| CN | 101619043 A | 1/2010 |
| WO | WO-2010/002845 A2 | 1/2010 |

OTHER PUBLICATIONS

Barber et. al., The New England Journal of Medicine, 2004, Massachusetts Medical Society, vol. 351, p. 2883.*
Beger et. al., World Journal of Surgery, 2003, Societe Internationale de Chirurugie, vol. 27, pp. 1075-1084.*
Chabner et. al., Nature Reviews Cancer, 2005, Nature Publishing Group, vol. 5, pp. 65-72.*
Leaf, Fortune, Mar. 9, 2004, Time Inc., pp. 1-13.*
Gatenby, Nature, 2009, Nature Publishing Group, vol. 459, pp. 508-509.*
Form PCT/ISA/210, mailed Aug. 25, 2011, for International Application No. PCT/CN2011/074637.

* cited by examiner

*Primary Examiner* — Sarah Pihonak
(74) *Attorney, Agent, or Firm* — Gorman IP Law, APC

(57) ABSTRACT

Provided are certain quinazoline compounds, compositions thereof and methods of use thereof. These quinazoline compounds can effectively inhibit the overexpression and/or overactivity of epidermal growth factor receptor (EGFR).

10 Claims, No Drawings

QUINAZOLINE COMPOUNDS

This application is the National Stage Under 35 U.S.C. §371 of PCT International Application No. PCT/CN2011/074637 filed on May 25, 2011, which claims priority under 35 USC §119 of Application No. PCT/CN2010/074792 filed in China on Jun. 30, 2010. The entire contents of each of which are incorporated by reference.

TECHNICAL FIELD

The present invention relates to pharmaceutical field and, in particular, to certain quinazoline compounds, a composition containing said compounds and the use thereof. These quinazoline compounds can effectively inhibit the overexpression and/or overactivity of epidermal growth factor receptor (EGFR).

TECHNICAL BACKGROUND

Binding of epidermal growth factor (EGF) to epidermal growth factor receptor (EGFR) can activate tyrosine kinase activity and thereby may trigger reactions that lead to cellular proliferation. Over-expression and/or over-activity of EGFR may result in uncontrolled cell division which may be a predisposition for cancer. Compounds that can inhibit the over-expression and/or over-activity of EGFR are therefore potential candidates for treating cancer.

SUMMARY OF INVENTION

Provided is at least one compound chosen from
(3aR,6aR)—N-(4-(1-(3-fluorobenzyl)-1H-indazol-5-ylamino)-7-methoxyquinazolin-6-yl)-1-methylhexahydropyrrolo[3,4-b]pyrrole-5(1H)-carboxamide;
(3aS,6aS)—N-(4-(1-(3-fluorobenzyl)-1H-indazol-5-ylamino)-7-methoxyquinazolin-6-yl)-1-methylhexahydropyrrolo[3,4-b]pyrrole-5(1H)-carboxamide;
(3aR,6aR)—N-(4-(3-ethynylphenylamino)-7-methoxyquinazolin-6-yl)-1-methyl-hexahydropyrrolo[3,4-b]pyrrole-5(1H)-carboxamide;
(3aS,6aS)—N-(4-(3-chloro-4-(3-fluorobenzyloxy)phenylamino)-7-methoxyquinazolin-6-yl)-1-methylhexahydropyrrolo[3,4-b]pyrrole-5(1H)-carboxamide;
(3aR,6aR)—N-(4-(3-chloro-4-(3-fluorobenzyloxy)phenylamino)-7-methoxyquinazolin-6-yl)-1-methylhexahydropyrrolo[3,4-b]pyrrole-5(1H)-carboxamide;
(3aS,6aS)—N-(4-(3-chloro-4-(3-fluorobenzyloxy)phenylamino)quinazolin-6-yl)-1-methylhexahydropyrrolo[3,4-b]pyrrole-5(1H)-carboxamide; and
(3aR,6aR)—N-(4-(3-chloro-4-(3-fluorobenzyloxy)phenylamino)quinazolin-6-yl)-1-methylhexahydropyrrolo[3,4-b]pyrrole-5(1H)-carboxamide,
and/or at least one pharmaceutically acceptable salt thereof.

Also provided is a pharmaceutical composition comprising at least one pharmaceutically acceptable carrier and at least one compound and/or at least one pharmaceutically acceptable salt thereof described herein.

Also provided is a method of treating cancer responsive to inhibition of overexpression and/or overactivity of epidermal growth factor receptor, comprising administering to a subject in need thereof an effective amount of at least one compound and/or at least one pharmaceutically acceptable salt thereof described herein.

Also provided is a use of the compound of the invention and/or at least one pharmaceutically acceptable salt thereof in the preparation of a medicine for treating cancer. In a preferred embodiment, the cancer is chosen from lung cancer, head and neck cancer, colorectal cancer, pharynx cancer, epidermoid cancer, and pancreatic cancer.

Further provided is a method of inhibiting overexpression and/or overactivity of epidermal growth factor receptor comprising contacting epidermal growth factor receptor with an effective amount of at least one compound and/or at least one pharmaceutically acceptable salt thereof.

DETAILED DESCRIPTION OF INVENTION

As used in the present specification, the following words, phrases and symbols are generally intended to have the meanings as set forth below, except to the extent that the context in which they are used indicates otherwise. The following abbreviations and terms have the indicated meanings throughout:

Compounds described herein include, but are not limited to, their optical isomers, racemates, and other mixtures thereof. In those situations, the single enantiomers or diastereomers, i.e., optically active forms, can be obtained by asymmetric synthesis or by resolution of the racemates or mixtures of diastereomers. Resolution of the racemates or mixtures of diastereomers can be accomplished, for example, by conventional methods such as crystallization in the presence of a resolving agent, or chromatography, using, for example a chiral high-pressure liquid chromatography (HPLC) column.

Where compounds described herein exist in various tautomeric forms, the term "compound" is intended to include all tautomeric forms of the compound. Such compounds also include crystal forms including polymorphs and clathrates. Similarly, the term "salt" is intended to include all isomers, racemates, other mixtures, Z- and E-forms, tautomeric forms and crystal forms of the salt of the compound.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, HOOC—$(CH_2)_n$—COOH where n is 0-4, and like salts. Similarly, pharmaceutically acceptable cations include, but are not limited to sodium, potassium, calcium, aluminum, lithium, and ammonium.

In addition, if a compound described herein is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

A "solvate," such as a "hydrate," is formed by the interaction of a solvent and a compound. The term "compound" is intended to include solvates, including hydrates, of compounds. Similarly, "salts" includes solvates, such as hydrates, of salts. Suitable solvates are pharmaceutically acceptable solvates, such as hydrates, including monohydrates and hemi-hydrates.

A "chelate" is formed by the coordination of a compound to a metal ion at two (or more) points. The term "compound" is intended to include chelates of compounds. Similarly, "salts" includes chelates of salts.

A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding). Such non-covalent complexes are included in the term "compound'.

The term "active agent" is used to indicate a chemical substance which has biological activity. In some embodiments, an "active agent" is a chemical substance having pharmaceutical utility.

"Treating" or "treatment" or "alleviation" refers to administering at least one compound and/or at least one pharmaceutically acceptable salt described herein to a subject that has a disease or disorder, or has a symptom of a disease or disorder, or has a predisposition toward the disease or disorder, with the purpose to alleviate, relieve, alter, remedy, ameliorate, improve, or affect the disease or disorder, the symptoms of the disease or disorder, or the predisposition toward the disease or disorder. The disease or disorder can be, for example, cancer.

The term "inhibition" indicates a decrease in the baseline activity of a biological activity or process. "Inhibition of overexpression and/or overactivity of epidermal growth factor receptor," refers to a decrease in the expression and/or activity of EGFR as a direct or indirect response to the presence of at least one compound and/or at least one pharmaceutically acceptable salt described herein, relative to the activity of EGFR in the absence of the at least one compound and/or the at least one pharmaceutically acceptable salt thereof. The decrease in activity may be due to the direct interaction of the at least one compound and/or at least one pharmaceutically acceptable salt described herein with EGFR, or due to the interaction of the at least one compound and/or at least one pharmaceutically acceptable salt described herein, with one or more other factors that in turn affect EGFR activity. For example, the presence of at least one compound and/or at least one pharmaceutically acceptable salt described herein, may decrease EGFR activity by directly binding to the EGFR, by causing (directly or indirectly) another factor to decrease EGFR activity, or by (directly or indirectly) decreasing the amount of EGFR present in the cell or organism.

The term "effective amount" refers to an amount of at least one compound and/or at least one pharmaceutically acceptable salt described herein effective to "treat" a disease or disorder in a subject. In the case of cancer, the effective amount may cause any of the changes observable or measurable in a subject as described in the definition of "treating," "treatment" and "alleviation" above. For example, the effective amount can reduce the number of cancer or tumor cells; reduce the tumor size; inhibit or stop tumor cell infiltration into peripheral organs including, for example, the spread of tumor into soft tissue and bone; inhibit and stop tumor metastasis; inhibit and stop tumor growth; relieve to some extent one or more of the symptoms associated with the cancer, reduce morbidity and mortality; improve quality of life; or a combination of such effects. An effective amount may be an amount sufficient to decrease the symptoms of a disease responsive to inhibition of overexpression and/or overactivity of epidermal growth factor receptor. For cancer therapy, efficacy in vivo can, for example, be measured by assessing the duration of survival, time to disease progression (TTP), the response rates (RR), duration of response, and/or quality of life. Effective amounts may vary, as recognized by those skilled in the art, depending on route of administration, excipient usage, and co-usage with other agents.

The term "effective amount" may also refer to an amount of at least one compound and/or at least one pharmaceutically acceptable salt described herein effective to inhibit overexpression and/or overactivity of epidermal growth factor receptor.

The details of one or more embodiments of the disclosure are set forth below.

Provided is at least one compound chosen from
(3aR,6aR)—N-(4-(1-(3-fluorobenzyl)-1H-indazol-5-ylamino)-7-methoxyquinazolin-6-yl)-1-methylhexahydropyrrolo[3,4-b]pyrrole-5(1H)-carboxamide;
(3aS,6aS)—N-(4-(1-(3-fluorobenzyl)-1H-indazol-5-ylamino)-7-methoxyquinazolin-6-yl)-1-methylhexahydropyrrolo[3,4-b]pyrrole-5(1H)-carboxamide;
(3aR,6aR)—N-(4-(3-ethynylphenylamino)-7-methoxyquinazolin-6-yl)-1-methyl-hexahydropyrrolo[3,4-b]pyrrole-5(1H)-carboxamide;
(3aS,6aS)—N-(4-(3-chloro-4-(3-fluorobenzyloxy)phenylamino)-7-methoxyquinazolin-6-yl)-1-methylhexahydropyrrolo[3,4-b]pyrrole-5(1H)-carboxamide;
(3aR,6aR)—N-(4-(3-chloro-4-(3-fluorobenzyloxy)phenylamino)-7-methoxyquinazolin-6-yl)-1-methylhexahydropyrrolo[3,4-b]pyrrole-5(1H)-carboxamide;
(3aS,6aS)—N-(4-(3-chloro-4-(3-fluorobenzyloxy)phenylamino)quinazolin-6-yl)-1-methylhexahydropyrrolo[3,4-b]pyrrole-5(1H)-carboxamide; and
(3aR,6aR)—N-(4-(3-chloro-4-(3-fluorobenzyloxy)phenylamino)quinazolin-6-yl)-1-methylhexahydropyrrolo[3,4-b]pyrrole-5(1H)-carboxamide,
and/or at least one pharmaceutically acceptable salt thereof.

The quinazoline compounds and/or the pharmaceutically acceptable salts thereof described herein, can be synthesized from commercially available starting materials by methods well known in the art. The detailed processes are illustrated in the Example section of this application.

Synthetic chemistry transformations useful in synthesizing desirable quinazoline compounds are also described, for example, in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The at least one compound and/or at least one pharmaceutically acceptable salt described herein, can be purified by column chromatography, high performance liquid chromatography, crystallization, or other suitable methods.

The at least one quinazoline compound and/or at least one pharmaceutically acceptable salts thereof described herein, can interact with EGFR kinase and/or inhibit EGFR activity.

Also provided is a composition comprising at least one pharmaceutically acceptable carrier and at least one compound and/or at least one pharmaceutically acceptable salt described herein.

The composition comprising at least one compound and/or at least one pharmaceutically acceptable salt described herein, can be administered in various known manners, such as orally, parenterally, by inhalation spray, or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

An oral composition can be any orally acceptable dosage form including, but not limited to, tablets, capsules, emulsions and aqueous suspensions, dispersions and solutions. Commonly used carriers for tablets include lactose and corn starch. Lubricating agents, such as magnesium stearate, are also typically added to tablets. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A sterile injectable composition (e.g., aqueous or oleaginous suspension) can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the pharmaceutically acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or di-glycerides). Fatty acids, such as oleic acid and its glyceride derivatives are useful in the preparation of injectables, as are natural pharmaceutically-acceptable oils, such as olive oil or castor oil, such as in their polyoxyethylated versions. These oil solutions or suspensions can also contain a long-chain alcohol diluent or dispersant, or carboxymethyl cellulose or similar dispersing agents.

An inhalation composition can be prepared according to techniques well known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art.

A topical composition can be formulated in form of oil, cream, lotion, ointment and the like. Suitable carriers for the composition include vegetable or mineral oils, white petrolatum (white soft paraffin), branched chain fats or oils, animal fats and high molecular weight alcohols (greater than C12). In some embodiments, the pharmaceutically acceptable carrier is one in which the active ingredient is soluble. Emulsifiers, stabilizers, humectants and antioxidants may also be included as well as agents imparting color or fragrance, if desired. Additionally, transdermal penetration enhancers may be employed in these topical formulations. Examples of such enhancers can be found in U.S. Pat. Nos. 3,989,816 and 4,444,762.

Creams may be formulated from a mixture of mineral oil, self-emulsifying beeswax and water in which mixture the active ingredient, dissolved in a small amount of an oil, such as almond oil, is admixed. An example of such a cream is one which includes about 40 parts water, about 20 parts beeswax, about 40 parts mineral oil and about 1 part almond oil. Ointments may be formulated by mixing a solution of the active ingredient in a vegetable oil, such as almond oil, with warm soft paraffin and allowing the mixture to cool. An example of such an ointment is one which includes about 30% by weight almond and about 70% by weight white soft paraffin.

A pharmaceutically acceptable carrier refers to a carrier that it is compatible with active ingredients of the composition (and in some embodiments, capable of stabilizing the active ingredients) and not deleterious to the subject to be treated. For example, solubilizing agents, such as cyclodextrins (which form specific, more soluble complexes with the at least one compound and/or at least one pharmaceutically acceptable salt described herein), can be utilized as pharmaceutical excipients for delivery of the active ingredients. Examples of other carriers include colloidal silicon dioxide, magnesium stearate, cellulose, sodium lauryl sulfate, and D&C Yellow #10. Hydrophilic excipients such as synthetic and natural polymers (e.g. albumin and derivatives thereof), are also examples of pharmaceutically acceptable carriers.

Suitable in vitro assays can be used to preliminarily evaluate the efficacy of the at least one compound and/or at least one pharmaceutically acceptable salt described herein, in inhibiting the activity of EGFR. The at least one compound and/or at least one pharmaceutically acceptable salt described herein, can further be examined for its efficacy in treating cancers by in vivo assays. For example, the compounds described herein, and/or the pharmaceutically acceptable salts thereof, can be administered to an animal (e.g., a mouse model) having cancer and its therapeutic effects can be accessed. Based on the results, an appropriate dosage range and administration route for animals, such as humans, can also be determined.

Also provided is a method of treating cancer responsive to inhibition of overexpression and/or overactivity of epidermal growth factor receptor, comprising administering to a subject in need thereof an effective amount of at least one compound and/or at least one pharmaceutically acceptable salt described herein.

The at least one compound and/or at least one pharmaceutically acceptable salt described herein can be used to achieve a beneficial therapeutic or prophylactic effect, for example, in subjects with cancer. As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes, but is not limited to, solid tumors and bloodborne tumors. The term "cancer" encompasses diseases of skin, tissues, organs, bone, cartilage, blood, and vessels. The term "cancer" further encompasses primary and metastatic cancers.

Non-limiting examples of solid tumors include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; skin cancer, including e.g., malignant melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; soft tissue sarcoma; and thyroid carcinoma.

Non-limiting examples of hematologic malignancies include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed sideroblasts (RARS), (refractory anemia with excess blasts (RAEB), and RAEB in transformation (RAEB-T); and myeloproliferative syndromes.

In some embodiments, the examples of the cancer to be treated include, but are not limited to, lung cancer, head and neck cancer, colorectal cancer, pancreatic cancer, colon cancer, breast cancer, ovarian cancer, prostate cancer, stomach cancer, kidney cancer, liver cancer, brain cancer, bone cancer, and leukemia. In some embodiments, the examples of cancer to be treated are chosen from lung cancer, head and neck cancer, colorectal cancer, pharynx cancer, epidermoid cancer, and pancreatic cancer.

In some embodiments, the at least one compound and/or at least one pharmaceutically acceptable salt described herein, is administered in conjunction with an effective amount of another therapeutic agent that is different from said at least one compound and/or at least one pharmaceutically acceptable salt thereof described herein. In some embodiments, the other therapeutic agent is an anti-cancer agent. In some embodiments, the other therapeutic agent is one that is normally administered to patients with the disease or condition being treated. The at least one compound and/or at least one pharmaceutically acceptable salt described herein, may be administered with the other therapeutic agent in a single dosage form or as a separate dosage form. When administered as a separate dosage form, the other therapeutic agent may be administered prior to, at the same time as, or following administration of the at least one compound and/or at least one pharmaceutically acceptable salt described herein.

In some embodiments, at least one compound and/or at least one pharmaceutically acceptable salt described herein, is administered in conjunction with an anti-cancer agent. As used herein, the term "anti-cancer agent" refers to any agent that is administered to a subject with cancer for purposes of treating the cancer. Nonlimiting examples anti-cancer agents include: radiotherapy; immunotherapy; DNA damaging chemotherapeutic agents; and chemotherapeutic agents that disrupt cell replication.

Non-limiting examples of DNA damaging chemotherapeutic agents include topoisomerase I inhibitors (e.g., irinotecan, topotecan, camptothecin and analogs or metabolites thereof, and doxorubicin); topoisomerase II inhibitors (e.g., etoposide, teniposide, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, and carboplatin); DNA intercalators and free radical generators such as bleomycin; and nucleoside mimetics (e.g., 5-fluorouracil, capecitibine, gemcitabine, fludarabine, cytarabine, mercaptopurine, thioguanine, pentostatin, and hydroxyurea).

Chemotherapeutic agents that disrupt cell replication include: paclitaxel, docetaxel, and related analogs; vincristine, vinblastin, and related analogs; thalidomide and related analogs (e.g., CC-5013 and CC-4047); protein tyrosine kinase inhibitors (e.g., imatinib mesylate and gefitinib); proteasome inhibitors (e.g., bortezomib); NF-kappa B inhibitors, including inhibitors of I kappa B kinase; antibodies which bind to proteins overexpressed in cancers and thereby downregulate cell replication (e.g., trastuzumab, rituximab, cetuximab, and bevacizumab); and other inhibitors of proteins or enzymes known to be upregulated, over-expressed or activated in cancers, the inhibition of which downregulates cell replication.

Also provided is a method of inhibiting over-expression and/or over-activity of epidermal growth factor receptor comprising contacting epidermal growth factor receptor with an effective amount of at least one compound and/or at least one pharmaceutically acceptable salt described herein.

EXAMPLES

The following examples are intended to illustrate the disclosure without however limiting the scope thereof.

In the following examples, the abbreviations below are used:

AcOH acetic acid
CMC-Na carboxymethyl cellulose sodium
DELFIA Dissociation-Enhanced Lanthanide Fluorescent Immunoassay
DMEM Dulbecco's Modified Eagle's Medium
DMF N,N-Dimethylformamide
DMSO Dimethyl sulfoxide
DTT Dithiothreitol
EDTA ethylenediaminetetraacetic acid
EtOAc ethyl acetate
FBS fetal bovine serum
h hour(s)
mL milliliter(s)
min minute(s)
PBS phosphate buffered saline
PE petroleum ether
PMSF phenylmethanesulfonylfluoride
Py pyridine
THF tetrahydrofuran
Tris-Cl hydroxymethylaminomethane hydrochloride Example 1

(3aR,6aR)—N-(4-(1-(3-fluorobenzyl)-1H-indazol-5-ylamino)-7-methoxyquinazolin-6-yl)-1-methyl-hexahydropyrrolo[3,4-b]pyrrole-5(1H)-carboxamide Compound 1 was prepared according to the following scheme.

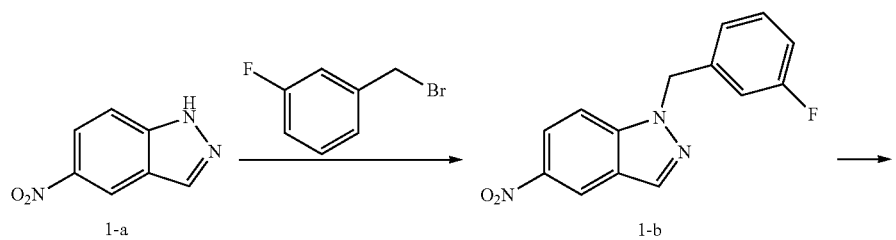

-continued
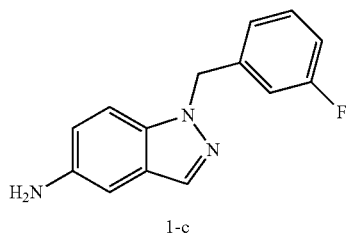
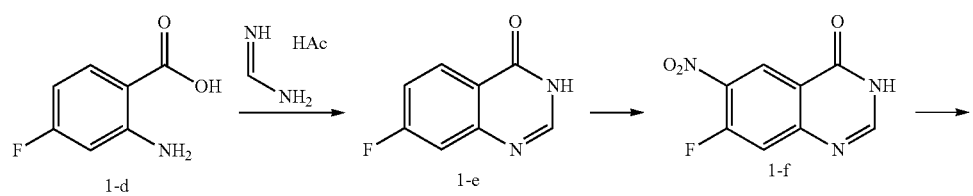
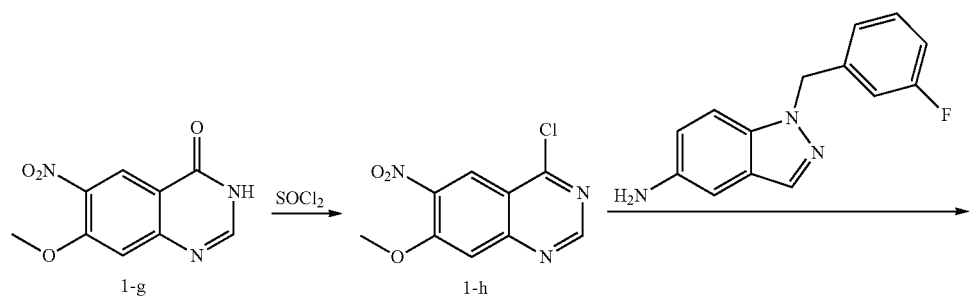
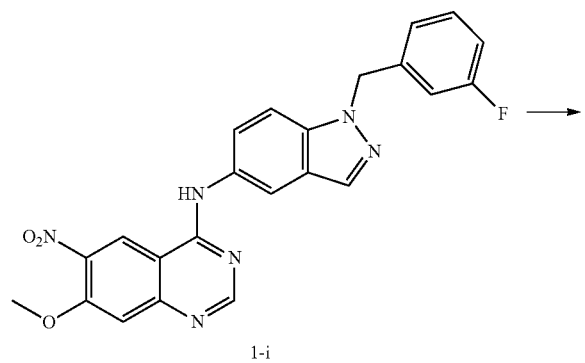
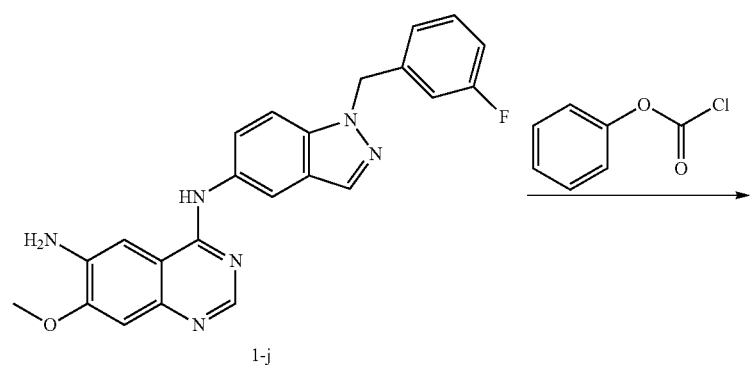

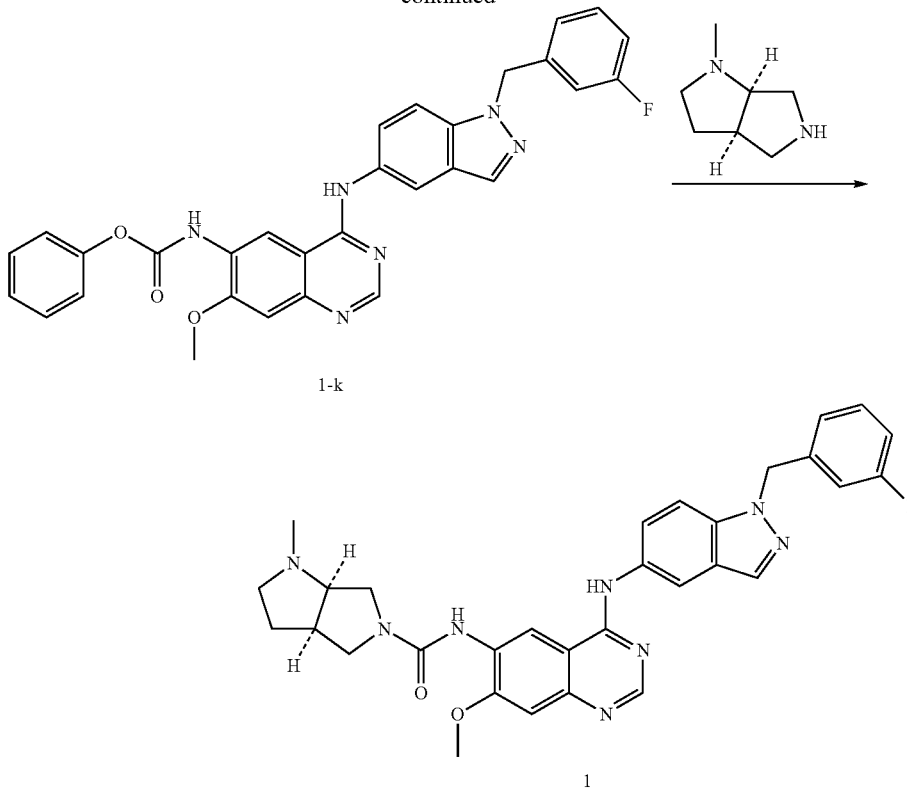

A mixture of 5-nitro-1H-indazole (1-a, 5 g, 30.65 mmol), 1-(bromomethyl)-3-fluorobenzene (3.76 mL, 30.65 mmol) and potassium carbonate powder (4.66 g, 30.65 mmol) in DMF (3 mL) was stirred at 80° C. for 3 h and then poured into water (100 mL). The precipitates were obtained by filtration and further purified by chromatography on silica gel (PE/EtOAc=3:1) to give 1-b (5.3 g, 19.7 mmol).

Under $N_2$, Raney's nickel (0.53 g, wet weight) was added to a solution of 1-b (5.3 g, 19.7 mmol) in methanol (20 mL) and the mixture was degassed and stirred under hydrogen atmosphere at room temperature overnight. The catalyst was carefully filtered and the filtrate was concentrated in vacuum to give 1-c (4.65 g, 19.3 mmol).

A mixture of 2-amino-4-fluorobenzoic acid (1-d, 7.75 g, 50 mmol) and methanimidamide acetate (15.6 g, 150 mmol) in ethanol was stirred at refluxing temperature overnight, and then cooled to the ambient temperature. The precipitates were filtered and dried in vacuum to give 1-e (8.0 g, 48 mmol).

7-Fluoroquinazolin-4(3H)-one (1-e, 8.0 g, 48 mmol) was dissolved in concentrated $H_2SO_4$ (24 mL) and the solution was cooled to 0° C. in an ice bath. $HNO_3$ (24 mL) was then added to the above solution dropwise to keep the reaction temperature below 0° C. The mixture was then slowly heated to 100° C. and stirred for 3 days. The resulting mixture was cooled to the ambient temperature and poured into ice water. The precipitates were obtained by filtration and then recrystallized in AcOH to give 1-f (3.25 g, 15.53 mmol).

Under $N_2$, metal sodium (0.71 g, 31 mmol) was carefully added to methanol (anhydrous, 100 mL) and stirred for 10 minutes to prepare fresh sodium methoxide solution. To the above solution, 7-fluoro-6-nitroquinazolin-4(3H)-one (1-f, 3.25 g, 15.53 mmol) was then added and the mixture was heated to reflux for 3 h. The resulting mixture was cooled to the ambient temperature and acidified with HCl (2 N) until pH=3-4. The volatiles were removed under reduce pressure. The residue was suspended in water, and the solid was collected by filtration and dried in vacuum to give 1-g (3.17 g, 14.4 mmol).

DMF (0.5 mL) was added to a solution of 7-methoxy-6-nitroquinazolin-4(3H)-one (1-g, 1.23 g, 5.56 mmol) in $SOCl_2$ (8 mL) and the mixture was heated to reflux for 4 h. The volatiles were removed under reduced pressure to give (1-h, 1.2 g, 5.0 mmol).

A mixture of 4-chloro-7-methoxy-6-nitroquinazoline (1-h, 1.2 g, 5.02 mmol) and 1-(3-fluorobenzyl)-1H-indazol-5-amine (1-c, 1.2 g, 4.98 mmol) in dioxane (40 mL) was heated to reflux for 3 h. It was then cooled to the ambient temperature. The precipitates were obtained by filtration and purified by chromatography on silica gel to give 1-i (1.7 g, 3.88 mmol) as a yellow solid.

Under $N_2$, Raney's nickel (0.13 g, wet weight) was added to a solution of 1-i (1.5 g, 3.7 mmol) in methanol (20 mL). The suspension was degassed and purged with $H_2$ three times, and then stirred under hydrogen atmosphere at room temperature for 4 h. The catalyst was carefully filtered off. The filtrate was concentrated in vacuum to give 1-j (1.36 g, 3.29 mmol) as a yellow solid.

To a solution of 1-j (1.36 g, 3.29 mmol) and pyridine (0.78 g, 9.86 mmol) in DMF (3 mL) was added phenyl carbonochloridate (1.53 g, 9.86 mmol). The mixture was stirred at room temperature for 1 h. The precipitates were obtained by filtration and dried to give 1-k (1.40 g, 2.63 mmol).

A solution of 1-k (1.1 g, 2.2 mmol), pyridine (0.2 g, 2.6 mmol) and (3aR,6aR)-1-methyloctahydropyrrolo[3,4-b]pyrrole (0.33 g, 2.6 mmol) in DMF (3 mL) was stirred at 80° C. for 1 h, then poured into ice water, extracted with EtOAc (3×40 mL). The combined extracts were washed with brine, dried with $Na_2SO_4$ (anhydrous), filtered and concentrated. The residue was purified by chromatography on silica gel (EtOAc/methanol=2:1) to give compound 1 (0.79 g, 1.4 mmol). MS (m/e): 567.1 (M+1)⁺.

Example 2

(3aS,6aS)—N-(4-(1-(3-fluorobenzyl)-1H-indazol-5-ylamino)-7-methoxyquinazolin-6-yl)-1-methyl-hexahydropyrrolo[3,4-b]pyrrole-5(1H)-carboxamide

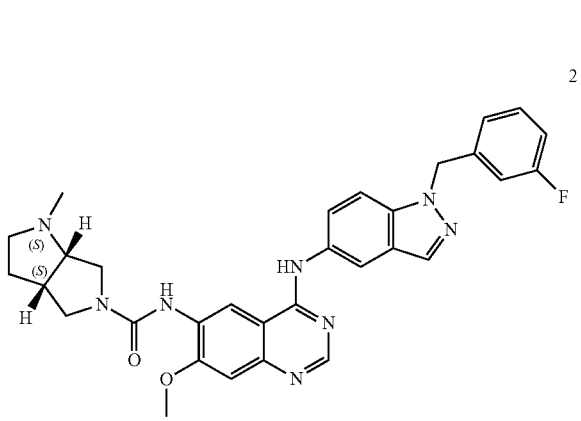

Compound 2 was prepared according to the procedures of Example 1 under similar conditions using (3aS,6aS)-1-methyloctahydropyrrolo[3,4-b]pyrrole. MS (m/e): 566.8 (M+1)⁺.

Example 3

(3aR,6aR)—N-(4-(3-ethynylphenylamino)-7-methoxyquinazolin-6-yl)-1-methyl-hexahydropyrrolo[3,4-b]pyrrole-5(1H)-carboxamide

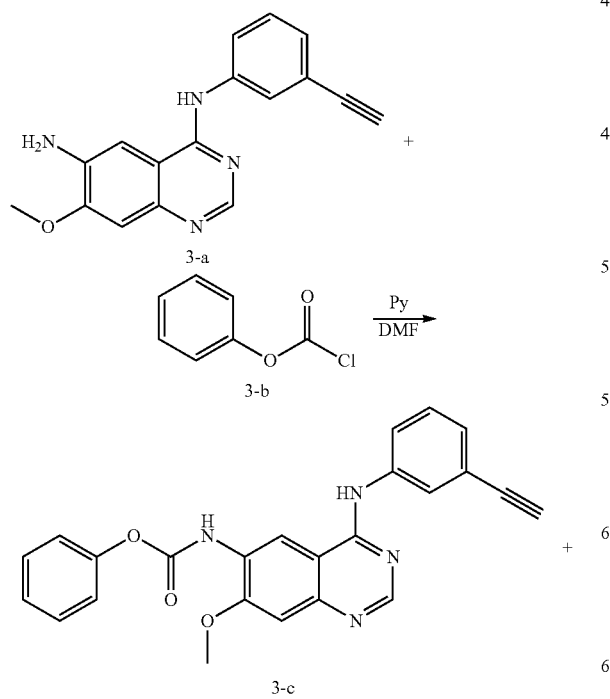

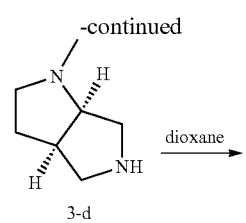

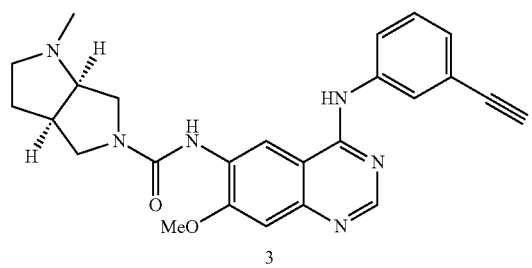

To a solution of Compound 3-a (40 g, 0.138 mol, prepared according to procedures disclosed in WO2010002845), pyridine (40 mL, 0.495 mol) and DMF (anhydrous, 22 mL) in anhydrous THF (500 mL), was added phenyl carbonochloridate 3-b (22 mL, 0.175 mol) dropwise at −10° C. The mixture was stirred at room temperature for 12 hours. The precipitates were filtered and then suspended in saturated NaHCO₃ solution (500 mL). The solid was filtered, washed with H₂O and EtOAc, and dried in vacuum to give compound 3-c (46 g). A mixture of compound 3-c (1 g, 2.44 mmol) and compound 3-d (369 mg, 2.92 mmol) in dioxane (30 mL) was stirred at 70° C. for 5 hours, and then cooled to the ambient temperature. The precipitates were filtered, washed with EtOAc, and dried in vacuum to give compound 3 (0.8 g). MS (m/e): 443.4 (M+1)⁺.

Example 4

(3aS,6aS)—N-(4-(3-chloro-4-(3-fluorobenzyloxy)phenylamino)-7-methoxyquinazolin-6-yl)-1-methyl-hexahydropyrrolo[3,4-b]pyrrole-5(1H)-carboxamide

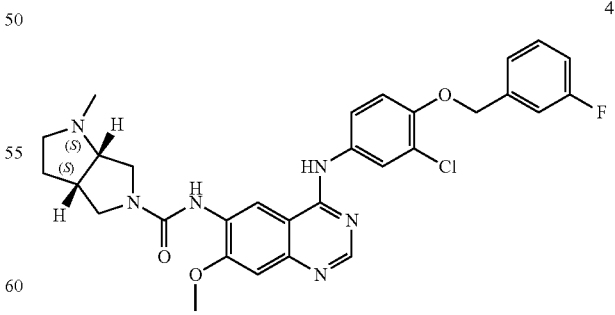

Compound 4 was prepared according to the procedures of Example 2.

MS (m/e): 576.9 (M+1)⁺

Example 5

(3aR,6aR)—N-(4-(3-chloro-4-(3-fluorobenzyloxy)phenylamino)-7-methoxyquinazolin-6-yl)-1-methylhexahydropyrrolo[3,4-b]pyrrole-5(1H)-carboxamide

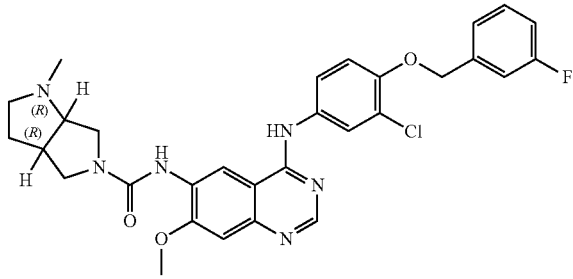

Compound 5 was prepared according to the procedures of Example 1.
MS (m/e): 576.7 (M+1)$^+$

Example 6

(3aS,6aS)—N-(4-(3-chloro-4-(3-fluorobenzyloxy)phenylamino)quinazolin-6-yl)-1-methylhexahydropyrrolo[3,4-b]pyrrole-5(1H)-carboxamide

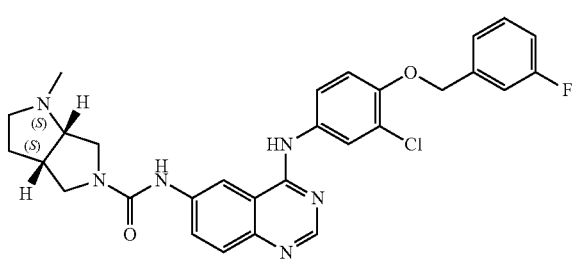

Compound 6 was prepared according to the procedures of Example 2.
MS (m/e): 546.8 (M+1)$^+$

Example 7

(3aR,6aR)—N-(4-(3-chloro-4-(3-fluorobenzyloxy)phenylamino)quinazolin-6-yl-1-methylhexahydropyrrolo[3,4-b]pyrrole-5(1H)-carboxamide

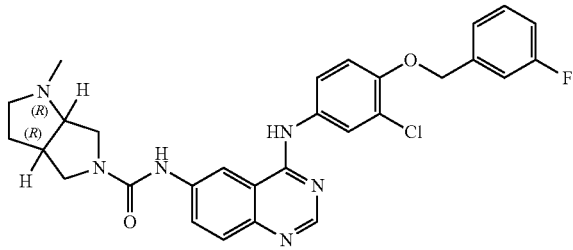

Compound 7 was prepared according to the procedures of Example 1.
MS (m/e): 546.8 (M+1)$^+$

Pharmacological Tests

EGFR Activation-Inhibiting Test

Cell seeding and starving: A431 (human epidermoid carcinoma) cells diluted in 10% PBS containing DMEM are seeded at $1.3 \times 10^4$ cells/well in 96-well plates and incubated overnight. Then the cell culture medium is replaced with 90 μL/well serum-free DMEM medium. The plates are incubated overnight for starvation.

Compound dilution and treatment: the test compounds are diluted in a 3-fold series in FBS-free medium containing 5% DMSO. 10 μL/well of the diluted compound is added into cells, 10 μL/well of 5% DMSO without test compound is added into the control wells. Duplication study is performed for each test point. Then, the plates are incubated at 37° C. for 60 minutes in a 5% $CO_2$ incubator. 10 μL/well of 200 ng/mL EGF (Biosource, PHG0064) is added and incubate the plates at 37° C. for 45 minutes in the 5% $CO_2$ incubator.

Lysate preparation: the medium is removed, and 100 μL/well of 50 mM Tris-Cl, pH 8.0 cell lysis buffer (containing 0.5 M NaCl, 0.2 mM EDTA, 0.1% Triton X-100, 1 μg/mL aprotinin, 0.75 μg/mL leupeptin, 1 μg/mL pepstatin, 1 mM DTT, 500 μM sodium vanadate, and 1 mM PMSF) is added into each well to lyse cells. The protease inhibitors are added right before use. The cell lysate is frozen at −80° C. overnight.

Plate coating and blocking: 100 μL/well of 0.5 μg/ml anti-EGFR antibody (Perkin Elmer, AF231) diluted in PBS is added to a 96-well DELFIA plate (Perkin Elmer, AAAND-0001) and incubated at 25° C. overnight with gentle shaking. The solution is discarded. The plate is washed 3 times with 200 μL/well of DELFIA wash buffer (PBS buffer containing 0.05% Tween-20). 200 μL/well of blocking buffer (PBS containing 0.137 M of NaCl, 0.0027 M of KCl, 0.01 M of $Na_2PO_4 \cdot 12H_2O$, 0.0015 M of $KH_2PO_4$, pH7.4, and 1% BSA) is added into each well and the plate is incubated at 25° C. for 2 h with gentle shaking.

Binding: the blocking buffer is discarded and the plate is washed with 200 μL/well of DELFIA wash buffer 3 times. 80 μL/well of the sample diluent (20 mM Tris-Cl/pH7.3, 150 mM NaCl, 0.1% of BSA, and 0.05% Tween-20) and 20 μL/well of cell lysate are then added to each well. Incubate the plate at 25° C. for additional 1 h with gentle shaking.

Detection: The plate is washed again with 200 μL/well of DELFIA wash buffer for 3 times. 100 μL/well of 0.5 mg/ml Eu-PT66 antibody (Perkin Elmer, AD0040) diluted in DELFIA assay buffer (Perkin Elmer, 1244-106) is added and incubate the plate at 25° C. for 1 h with gentle shaking. After washing with 200 μL/well of DELFIA wash buffer 3 times, 100 μL/well of DELFIA enhancement buffer (Perkin Elmer, 4001-0010) is added. Incubate the plate at 25° C. for 30 min with gentle shaking.

Readout: fluorescence signal is measured at 340 nm excitation and 620 nm emission on Victor$^3$ (PerkinElmer).

Inhibition rates are calculated as follow:

$$\text{Inhibition (\%)} = 100 - \frac{[\text{Fluorescence Readout}]_{Treated} - [\text{Fluorescence Readout}]_{Untreated}}{[\text{Fluorescence Readout}]_{EGF} - [\text{Fluorescence Readout}]_{Untreated}} \times 100$$

Where,

[Fluorescence Readout]$_{Treated}$ is the readout of the wells treated with test compound upon EGF stimulation

[Fluorescence Readout]$_{Untreated}$ is the readout of the wells with neither compound treatment nor EGF stimulation, which is used as cell background signal

[Fluorescence Readout]$_{EGF}$ is the readout of wells with EGF stimulation, but no compound treatment, which is used as maximal signal IC$_{50}$ is calculated using XL-Fit 2.0 software.

IC$_{50}$ values of compounds 1-7 are 0.185, 0.439, 0.006, 0.016, 0.044, 0.210, and 0.241 uM, respectively.

In Vivo Anti-Tumor Tests in Human Xenograft Models

1. Materials and Methods:

Human tumor cell lines: Fadu (human head and neck, pharynx carcinoma, HTB-43), HCC827 (human non small cell lung cancer, NSCLC; CRL-2868), A431 (human epidermoid carcinoma, CRL-2592) cell lines were purchased from ATCC; Fadu, HCC827 and A431 cells were grown in EMEM, RPMI 1640 and DMEM medium plus 10% FBS respectively. These cells were incubated in a humidifier incubator at 37° C. and under 5% $CO_2$.

Animals: Athymic mice (6-8 weeks) were purchased from Shanghai SLAC laboratory animal CO. LTD. The animals were housed in the SPF environment, 4 animals/cage under standard conditions (12:12 h light/dark, 40-50% relative humidity at 20-25° C.) and were given free access to $Co^{60}$ radiated-sterile diet and sterile water.

Agents: Test compounds were formulated in sterile 0.5% CMC-Na at different concentrations (0.05~1.0 mg/mL), and then stored at 4° C.

Subcutaneous implantation of tumor cells and anti-tumor efficacy study: The tumor cells were incubated at 37° C. in a 5% $CO_2$ incubator until they reached approximately 80% confluence. Cells were detached by 0.05% Trypsin-EDTA, centrifuged at 800 rpm, and the cells were suspended in serum free medium. The concentration was adjusted for nude mice implantation. The nude mice were quarantined for several days before implantation, and $3 \times 10^6$ FaDu or A431 cells in 0.1 mL medium, or $5 \times 10^6$ HCC827 cells in the 0.2 mL medium were subcutaneously injected to the right lateral flank of nude mice.

One to three weeks after inoculation, when average tumor volume reached 100-300 mm$^3$, the animals were randomized and divided into vehicle and compound treated groups. The mice were orally administrated with either the vehicle, 0.5% CMC-Na, or the test compounds at different dose levels once a day. The dosing volume was 10 mL/kg body weight (dosing regimen was shown in Table 1 and Table 2). Tumor volume was measured 2-3 times per week by caliper for length and width, and was calculated using the formula: Tumor volume (TV, mm$^3$)=width$^2$×length/2. Animal body weight and behavior were observed during the experiment. Tumor growth inhibition was calculated as follows: TGI (%)=100− (T−T$_0$)/(C−C$_0$)×100%, where T represents mean tumor volume of a treated group on a specific day during the experiment, T$_0$ represents mean tumor volume of the same treated group on the first day of treatment, C represents mean tumor volume of a control group on the specific day during the experiment, and C$_0$ represents mean tumor volume of the same control group on the first day of treatment.

TABLE 1

Dosing regimen of test compound in Fadu and A431 xenografts

| Group | Dosage regimens | Animal number (n) |
| --- | --- | --- |
| Vehicle | 0.5% CMC-Na, p.o., qd × 21 days | 8 |
| Test compound, 2 mg/kg | 2 mg/kg, p.o., qd × 21 days | 8 |
| Test compound, 5 mg/kg | 5 mg/kg, p.o., qd × 21 days | 8 |
| Test compound, 10 mg/kg | 10 mg/kg, p.o., qd × 21 days | 8 |

TABLE 2

Dosing regimen of Test compound in HCC827 xenograft

| Group | Dosage regimens | Animal number (n) |
| --- | --- | --- |
| Vehicle | 0.5% CMC-Na, p.o., qd × 21 days | 8 |
| Test compound, 0.5 mg/kg | 0.5 mg/kg, p.o., qd × 21 days | 8 |
| Test compound, 1 mg/kg | 1 mg/kg, p.o., qd × 21 days | 8 |
| Test compound, 2 mg/kg | 2 mg/kg, p.o., qd × 21 days | 8 |
| Test compound, 5 mg/kg | 5 mg/kg, p.o., qd × 21 days | 8 |

2. Statistic Analysis:

Tumor volume data were expressed as Mean±SD. One-way ANOVA was used for multiple comparisons and Student's t-test was used for comparison with vehicle control. Differences were considered statistically significant at $P<0.05$.

3. Results:

The test compound showed significant tumor growth inhibition in the three tumor models in a dosage-dependent manner. In addition, none of the mice treated with the test compound exhibited significant body weight loss during the experiments.

The TGIs (%) produced by the representative test compound, in Example 3 are shown in the table below.

TABLE 3

TGI % of compound 3 in subcutaneous human xenograft models

| | HCC827 | FaDu | A431 |
| --- | --- | --- | --- |
| 0.5 mpk | 59.2 | — | — |
| 1 mpk | 114.7 | — | — |
| 2 mpk | 127.8 | 46.1 | 21.3 |
| 5 mpk | 140.8 | 66.9 | 62.8 |
| 10 mpk | — | 95.2 | 85.3 | hERG Assay

1. Cell Culture

A CHO cell line stably transfected with hERG cDNA and expressing hERG channels was used for the study. Cells were cultured in medium containing:
  Dulbecco's Modified Eagle Medium (DMEM/F12)
  10% (v/v) heat inactivated Fetal Bovine Serum (FBS)
  1% (v/v) penicillin/streptomycin
  500 μg/ml Geneticin® reagent (G418)
Before testing, cells were harvested using an Accumax (Innovative Cell Technologies).

2. Solutions

For the electrophysiological recordings the following solutions were used

TABLE 4

Composition of internal and external solutions used in hERG patch clamp studies

| Reagent | External Solution (mM) | Internal Solution (mM) |
|---|---|---|
| $CaCl_2$ | 1.8 | — |
| $MgCl_2$ | 1.0 | 1 |
| KCl | 4 | 130 |
| NaCl | 137 | — |
| Glucose | 10 | — |
| HEPES | 10 | 10 |
| EGTA | — | 5 |
| ATP | — | 5 |
| pH | 7.4 (adjusted with NaOH), osmolarity ~280 mOsm | 7.25 (adjusted with KOH), osmolarity ~280 mOsm |

3. Recording System

Whole-cell recordings were performed using a EPC10 USB(HEKA). The cells were voltage clamped at a holding potential of −80 mV. The hERG current was activated by depolarizing at +20 mV for 2 sec, after which the current was taken back to −50 mV for 2 sec to remove the inactivation and observe the deactivating tail current. The first step at −50 mV was used as a baseline for measuring the tail current peak amplitude.

4. Compound Handing and Dilutions

Compounds were prepared as a 10 mM DMSO stock in a glass vial. The stock solution was mixed vigorously for 10 minute at room temperature. For testing, the compound was diluted in a glass vial using solution; the dilution was prepared no longer than 30 minutes before use. Equal amounts of DMSO (0.1%) were present at final dilution.

5. Electrophysiology Procedures

After achieving whole-cell configuration, the cells were monitored for 90 sec to assess stability and washed with external solution for 66 sec. The voltage protocol described above was then applied to the cells every 20 sec throughout the whole procedure. Only stable cells with recording parameters above threshold were allowed to enter the drug addition procedure.

External solution containing 0.1% DMSO (vehicle) was applied to the cells to establish the baseline. After allowing the current to stabilize for 3 minutes, compound was applied. Compound solution was added in 4 steps and the cells were kept in the test solution until the compound's effect reached a steady state or for a maximum of 6 min. Subsequently, the positive control (100 nM Cisapride) was added. Washout with external solution was performed until the recovery of the current reached a steady state.

6. Data Analysis

Data were analyzed using Pulsefit and Origin 7 (Originlab Corporation).

7. Result

Compound 3 inhibited the hERG tail currents with an $IC_{50}$ of 9.3±1.2 µM (five concentrations, 5×2) using manual whole-cell patch clamp assay.

The invention claimed is:

1. A compound that is (3aR,6aR)—N-(4-(3-ethynylphenylamino)-7-methoxyquinazolin-6-yl)-1-methyl-hexahydropyrrolo[3,4-b]pyrrole-5(1H)-carboxamide; or a pharmaceutically acceptable salt thereof.

2. A pharmaceutical composition comprising the compound according to claim 1 or a pharmaceutically acceptable salt thereof.

3. A method of treating cancer responsive to inhibition of overexpression and/or overactivity of epidermal growth factor receptor, comprising administering to a subject in need thereof an effective amount of (3aR,6aR)—N-(4-(3-ethynylphenylamino)-7-methoxyquinazolin-6-yl)-1-methyl-hexahydropyrrolo[3,4-b]pyrrole-5(1H)-carboxamide; or a pharmaceutically acceptable salt thereof, wherein the cancer is selected from the group consisting of lung cancer, non small cell lung cancer, head and neck cancer, pharynx cancer, an epidermoid cancer.

4. The method of claim 3, further comprising administering to said subject thereof an effective amount of an anti-cancer agent, wherein said anti-cancer agent is different from (3aR,6aR)—N-(4-(3-ethynylphenylamino)-7-methoxyquinazolin-6-yl)-1-methyl-hexahydropyrrolo[3,4-b]pyrrole-5(1H)-carboxamide, or a pharmaceutically acceptable salt thereof.

5. The method according to claim 3, wherein the cancer is lung cancer.

6. The method according to claim 3, wherein the cancer is non small cell lung cancer.

7. The method according to claim 3, wherein the cancer is head and neck cancer.

8. The method according to claim 3, wherein the cancer is pharynx cancer.

9. The method according to claim 3, wherein the cancer is epidermoid cancer.

10. A method of inhibiting over-expression and/or over-activity of epidermal growth factor receptor comprising contacting epidermal growth factor receptor with an effective amount of (3aR,6aR)—N-(4-(3-ethynylphenylamino)-7-methoxyquinazolin-6-yl)-1-methyl-hexahydropyrrolo[3,4-b]pyrrole-5(1H)-carboxamide, or a pharmaceutically acceptable salt thereof.

* * * * *